(12) United States Patent
Mizutani et al.

(10) Patent No.: US 7,534,235 B2
(45) Date of Patent: May 19, 2009

(54) INTERLABIAL PAD

(75) Inventors: Satoshi Mizutani, Kagawa (JP); Koichi Yamaki, Kagawa (JP); Yuki Noda, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 335 days.

(21) Appl. No.: 10/705,406

(22) Filed: Nov. 10, 2003

(65) Prior Publication Data
US 2004/0158219 A1    Aug. 12, 2004

Related U.S. Application Data

(63) Continuation of application No. PCT/JP02/04898, filed on May 21, 2002.

(30) Foreign Application Priority Data

| May 22, 2001 | (JP) | ............................. 2001-152403 |
| Oct. 19, 2001 | (JP) | ............................. 2001-321485 |

(51) Int. Cl.
*A61F 13/15* (2006.01)
(52) U.S. Cl. ............................. 604/385.17; 604/385.18; 604/385.01; 604/11; 604/18; 604/12
(58) Field of Classification Search ............ 604/385.17, 604/385.18, 385.01, 11–18
See application file for complete search history.

(56) References Cited

U.S. PATENT DOCUMENTS 4,595,392 A * 6/1986 Johnson et al. ........ 604/385.17

| D404,814 S | 1/1999 | Mayer |
| 5,868,727 A | 2/1999 | Barr et al. |
| 5,891,126 A | 4/1999 | Osborn, III et al. |
| 5,916,205 A | 6/1999 | Olson et al. |
| 6,131,736 A * | 10/2000 | Farris et al. ................. 206/440 |

FOREIGN PATENT DOCUMENTS

| EP | 888764 | 1/1999 |
| FR | 2703244 | 10/1994 |
| JP | 49-3722 | 1/1974 |

(Continued)

OTHER PUBLICATIONS

Mizutani, et al., "Interlabial Pad", U.S. Appl. No. 10/705,408, filed Nov. 10, 2003.

(Continued)

*Primary Examiner*—Jacqueline F. Stephens
(74) *Attorney, Agent, or Firm*—Darby & Darby P.C.

(57) ABSTRACT

The present invention relates to an interlabial pad can be sealed and attached to the female labia, which has a structure in capable of easily achieving a sealing attachment into the female labia.

A sheet body (2) is provided on an opposite side to a body side of the interlabial pad (1) to form a pair of the fingertip insert openings (3,4) on both side portions, the wearer inserts two finger into the fingertip insert opening (3,4) and catches the sheet body 2 by the two finger, thereby the interlabial pad (1) can be folded in substantially mountain folded shape along the vertically axial center line and can be attached to the labia (9) in keeping a condition of forming a raised area (5) on the body side surface of the pad.

10 Claims, 12 Drawing Sheets

FOREIGN PATENT DOCUMENTS

| | | |
|---|---|---|
| JP | 61-108258 | 7/1986 |
| JP | 63-260556 | 10/1988 |
| JP | 03-56366 | 3/1991 |
| JP | 5-237151 | 9/1993 |
| JP | 05-293138 A1 | 11/1993 |
| JP | 06-506368 | 7/1994 |
| JP | 06/40203 | 10/1994 |
| JP | 08-215242 A1 | 8/1996 |
| JP | 11-178849 A | 7/1999 |
| JP | 2000-008444 A | 1/2000 |
| JP | 2000-51267 | 2/2000 |
| JP | 2000501322 | 2/2000 |
| JP | 2001506170 | 5/2001 |
| JP | 2001506532 | 5/2001 |
| JP | 2001-509402 | 7/2001 |
| JP | 2001523522 | 11/2001 |
| JP | 2002-513633 A1 | 5/2002 |
| JP | 2002-534163 | 10/2002 |
| TW | 247431 A1 | 5/1995 |
| TW | 294591 A1 | 1/1997 |
| TW | 338315 A1 | 8/1998 |
| TW | 386030 A1 | 4/2000 |
| TW | 386872 A1 | 4/2000 |
| TW | 394681 A1 | 6/2000 |
| TW | 416847 A1 | 1/2001 |
| TW | 442278 A1 | 6/2001 |
| TW | 450802 A1 | 8/2001 |
| TW | 454503 A1 | 9/2001 |
| TW | 470640 A1 | 1/2002 |
| TW | 524677 A1 | 3/2003 |
| WO | WO-92/11825 A1 | 7/1992 |
| WO | 9422405 | 10/1994 |
| WO | WO-95/00094 | 1/1995 |
| WO | 95/17148 A2 | 6/1995 |
| WO | 9602217 | 2/1996 |
| WO | WO-98/08475 A1 | 3/1998 |
| WO | WO-98/57610 A1 | 12/1998 |
| WO | WO-99/01093 A1 | 1/1999 |
| WO | WO-99/01096 A1 | 1/1999 |
| WO | WO-99/26575 A1 | 6/1999 |
| WO | WO-99/44494 A1 | 9/1999 |
| WO | WO-99/56681 | 11/1999 |
| WO | WO-99/56689 A1 | 11/1999 |
| WO | WO-00/40192 | 7/2000 |
| WO | WO-01/47458 | 7/2001 |

OTHER PUBLICATIONS

Mizutani, et al., "Interlabial Pad", U.S. Appl. No. 10/705,780, filed Nov. 10, 2003.

Mizutani, et al., "Interlabial Pad and Package Thereof", U.S. Appl. No. 10/705,400, filed Nov. 10, 2003.

Mizutani, et al., "Interlabial Pad Individual Packaging Body", U.S. Appl. No. 10/705,669, filed Nov. 10, 2003.

Mizutani, et al., "Interlabial Pad", U.S. Appl. No. 10/705,811, filed Nov. 10, 2003.

Mizutani, et al., "Interlabial Pad", U.S. Appl. No. 10/705,812, filed Nov. 10, 2003.

Mizutani, et al., "Interlabial Pad", U.S. Appl. No. 10/705,399, filed Nov. 10, 2003.

Mizutani, et al., "Interlabial Pad Individual Packaging Vessel, and Individual Packaging Body", U.S. Appl. No. 10/705,781, filed Nov. 10, 2003.

Mizutani, et al., "Individual Packaging Body and Outer Vessel Therefor", U.S. Appl. No. 10/705,402, filed Nov. 10, 2003.

Mizutani, et al., "Interlabial Pad", U.S. Appl. No. 10/705,403, filed Nov. 10, 2003.

Mizutani, et al., "Interlabial Pad", U.S. Appl. No. 10/705,407, filed Nov. 10, 2003.

Mizutani, et al, "Interlabial Pad and Package", U.S. Appl. No. 10/706,303, filed Nov. 10, 2003.

Mizutani, et al., "Interlabial Pad and Package Thereof", U.S. Appl. No. 10/705,404, filed Nov. 10, 2003.

Mizutani, et al., "Interlabial Pad Individual Packaging Vessel", U.S. Appl. No. 10/705,673, filed Nov. 10, 2003.

Mizutani, Satoshi, "Interlabial Product Having Form for Finger Securement, and Individual Package", U.S. Appl. No. 10/705,779, filed Nov. 10, 2003.

Mizutani, et al., "Interlabial Pad and Package Thereof", U.S. Appl. No. 10/705,810, filed Nov. 10, 2003.

Mizutani, et al., "Flap-Equipped Interlabial Pad", U.S. Appl. No. 10/705,670, filed Nov. 10, 2003.

Mizutani, et al., "Interlabial Pad", U.S. Appl. No. 10/705,778, filed Nov. 10, 2003.

A Notice of Reason for Rejection, dated Oct. 30, 2007, which issued during the prosecution of Japanese Application No. 2002-253330 which corresponds to the present application.

A Notice of Reason for Rejection, dated Oct. 2, 2007, which issued during the prosecution of Japanese Application No. 2003-181920 which corresponds to the present application.

Notice of Reason for Rejection, dated Oct. 30, 2007, which issued during the prosecution of Japanese Application No. 2003-181922 which corresponds to the present application.

An Office Action, dated Nov. 2, 2007, which issued during the prosecution of European Application No. 03795252.0 which corresponds to the present application.

* cited by examiner (A)

(B)

(C) (D)

(A)

(B)

INTERLABIAL PAD

CROSS-REFERENCE TO RELATED APPLICATIONS

This application is a Continuation of International Application No. PCT/JP02/04898 filed May 21, 2002, which application published in Japanese on Nov. 28, 2002 as WO 02/094162 A1 under PCT Article 21(2).

BACKGROUND OF THE INVENTION

1. Technical Field

The present invention relates to an interlabial pad which can be sealed and attached to the labia of females.

2. Background Art

Conventionally, sheet type absorbent products like a sanitary napkin are used generally as female sanitary products to absorb body liquid such as menstrual blood. Here, there have been great efforts to prevent the leak of menstrual blood from gap caused by poor adhesion near the ostium vaginae as for the sanitary napkin.

However, since the sanitary napkin, used by being fixed to garments, has intrinsically poor adhesion near the ostium vaginae, position shift may occur between the underwear to which the sanitary napkin is fixed and the inner thigh due to the body action of the wearer, and an unnecessary gap generates sometimes.

Under such situation, sanitary products of the interlabial pad have attracted people as a sanitary product smaller than the sanitary napkin in recent years.

The interlabial pad is used by inserting its portion between the labia and bringing into contact with the inner face of labia, it prevents the menstrual blood from leaking because of higher adhesion to the body than that of the sanitary napkin, and the menstrual blood from bringing widely into contact with the body by diffusing, so it is sanitary and clean. Moreover, it has advantages that it excels in a feeling of wearing and is comfortable because of being smaller than the sanitary napkin.

However, interlabial pads have a drawback that it is more difficult to wear them than sanitary napkins because interlabial pads are worn between labia where it is hard to be viewed. Further, if an interlabial pad is not worn to an appropriate point, menstrual blood leakage results in immense damage because the interlabial pad is smaller than the sanitary napkin.

With regard to inventions in which amelioration of wearing troubles in interlabial pads is tried, PCT International Publication No. WO99/56689 discloses a pad that having a structure that a projection is formed on the opposite side to the body-contacting face. With this structure, a wearer can wear a pad by taking the projection with fingers. It is supposed that that this kind of pad can be worn more readily than a pad without a projection. (see FIG. 18)

However it is difficult to press the interlabial pad to the labia for sealing therewith sufficiently only by pinching the projection, moreover in a conventional interlabial pad, a surface of the pad contacting with the body has been plane-shaped, and the pad is difficult to be attached along the labia in form of a groove-shaped.

As described before, the conventional interlabial pad has not come to be capable of sealing with the labia completely. Furthermore it has been possible to cause a case as ever that the finger has been stained with the menstrual blood in wearing and to induce feeling of resistance to use the interlabial pad.

In respect of problems described hereinbefore, the object of the present invention is to provide an interlabial pad having a structure to allow wearing to seal with the female labia sanitarily.

SUMMARY OF THE INVENTION

To solve the problem described hereinbefore, the interlabial pad of the present invention, having a structure which comes to be a form of easily in accordance with the pudendal cleft in wearing the pad and can be wore in keeping the form, more concretely, the interlabial pad of the present invention is so constructed that a pair of openings to insert the finger is provided on both side portions of the interlabial pad, the interlabial pad is folded in a mountain-hold shape along a centerline of a vertical axis by hooking the tip of finger and can be wore into the interlabial in keeping the form.

In the embodiment of the present invention, the present invention provides the interlabial pad as follows;

(1) An interlabial pad, comprising: an absorbent body in capable of absorbing body liquid, said absorbent body being enclosed in the interlabial pad; a size capable of pinching thereof between labia naturally, and a shape including a longitudinal axis direction and a lateral axis direction, wherein a pair of fingertip insert openings having a size such that fingertips of a wearer are inserted naturally are provided in said interlabial pad, and said pair of fingertip insert openings are provided at a line symmetry position on both opposite sides of said interlabial pad with a center axis being said longitudinal axis direction, whereby in using the pad, each fingertip of two fingers of the wearer is inserted into said pair of fingertip insert openings respectively, and the interlabial pad is subject to use in a condition of being folded at a symmetric axis of said line symmetry.

According to the interlabial pad of the present invention, a pair of finger insertion openings are provided on both side portions of the pad for which at least the finger can insert, that is, which the wearer can hook her finger. Thereby in wearing the pad, the wearer hook her two fingers on the pair of openings and comes to pull two fingers each other, therefore she can fold the whole interlabial pad toward a longitudinal direction at the center of the lateral direction of the pad. Thereby the pad raises in a mountain folded shape against the body side to preliminarily form a shape for easily progressing to the oblong and groove-shaped labia. Thereafter the wearer keeps the condition of her fingertip, and the raised area caused by folding the pad is held the mountain folded shape. Therefore, the pad of the present invention is held between labia, and its folded and raised area is inserted into the ostium vaginae in the neighborhood of labia minora, which is at the deepest portion of labia. Thereby the clearance which is formed between the pad and labia can be decreased much to increase a sealing efficiency of the pad with labia and the occurrence of a leak of the menstrual blood can be prevented.

In accordance with the present invention, in wearing the pad, the fingertip is inserted into the fingertip insertion opening, thereby prevented from contacting directly with labia or the menstrual blood adhered thereon to perform the wearing action sanitarily.

The fingertip insertion opening may be suitable for inserting the at least fingertip, more preferably made so that the fingertip can be inserted deeply (See FIG. 5).

(2) An interlabial pad according to (1), wherein a size of the width of the fingertip insert opening is greater than 20 mm.

The interlabial pad of the present invention has the width of fingertip insertion opening which is suitable for inserting a flat-shaped fingertip of the wearer smoothly. Thereby the wearer is urged to insert the fingertip so as to contact the ball of finger with the sheet surface, and to hold the interlabial pad without an operation of rotating the inserted fingertip. Therefore the attachment of the pad can be achieved more rapidly.

In the specification of the present invention, the word "the width" of the fingertip insert opening means a size of the width of the opening portion of the opening (See FIG. 2).

(3) An interlabial pad according to (1) or (2), wherein a size of the depth of the fingertip insert opening is not less than 15 mm.

According to the interlabial pad of the present invention, in folding the interlabial pad by drawing fingertips which are inserted into the fingertip insert openings, the fingertip insert opening has a sufficient depth size so as to prevent fingertips from slipping out of the fingertip insert opening.

The fingertip insert openings may be connected a pair of fingertip insert openings located on the opposite side to form a tunnel (See FIG. 4 (A)).

In the present invention, "depth size" means a size of a straight line from the opening portion of the fingertip insert opening to a center portion of the lateral direction of the interlabial pad, which is an enough size to insert the fingertip which is inserted (See FIG. 4 (B)).

(4) An interlabial pad according to any one from (1) to (3), further comprising a sheet body being attached on an opposite side of said interlabial pad to a body side, said sheet body is attached to have a pair of unbonded portions on left and right side edge portions in respect of said longitudinal direction of said interlabial pad, and said pair of fingertip insert openings are formed by said pair of disconnect portions.

According to the interlabial pad of the present invention, a different sheet body from materials comprising the interlabial pad is attached on the opposite side to the body side. This attachment of the sheet body is made to have an unbonded portion on both side ends of the pad and the fingertip insert openings are formed on the unbonded portion. Thereby the wearer inserts two fingers into the fingertip insert opening respectively and only holds the sheet body, the sheet body held by fingers is drawn around the center portion and simultaneously the connecting area of the interlabial pad with the sheet body can cooperate with the actuation, so as to cause the function of folding the opposite side to the body side surface of the interlabial pad in facing with each other. Further in a body side surface of the interlabial pad, a mountain folded raising area toward the direction of the body is formed.

The sheet body and the interlabial pad may be bonded only on the peripheral edge of the interlabial pad except of the fingertip insert opening, or may be connected substantially through whole area of each other except for the fingertip insert opening.

(5) An interlabial pad according to (4), wherein said sheet body has a size not less than 80%, preferably a range of 80 to 130%, further preferably a range of 90 to 100% (which is the same size of the lateral direction of the interlabial direction) in respect of a length size of the lateral direction of the interlabial pad.

According to the interlabial pad of the present invention, in cooperating with picking the sheet body by the wearer, the size of the sheet body disposed on the opposite side to the body side is sufficient to fold the interlabial pad. Thereby only by picking the sheet body, the interlabial pad can be folded in a mountain folded shape surely to form the interlabial pad enabling of engaging along the pudendal cleft.

Herein, in the case that the length size of the sheet body is shorter than the length of the lateral direction of the interlabial pad, when the interlabial pad is so wrapped to expose the opposite side to the body side surface thereof at the time of breaking the seal of the wrapping container, the wearer can confirm the fingertip insert opening rapidly (See FIG. 6 (A)).

(6) An interlabial pad according to (4) or (5), wherein said sheet body has color, chromaticity, pattern different from those of the opposite side of the interlabial pad to the body side.

According to the interlabial pad of the present invention, the sheet body attached on the opposite side to the body side of the pad has a different color from the opposite side to the body side surface of the pad for identifying thereof from the opposite side to the body side surface of the pad by the wearer. Thereby the wearer can confirm the sheet body easily to catch the position of the fingertip insert opening which is formed between the sheet body and the interlabial pad.

In the present invention, the coloring or the pattern may be applied to indicate the position of the fingertip insert opening, therefore it is not necessary to apply the color or the pattern to both "a rear surface side sheet which is positioned at the opposite side to the body side of the pad" for forming the fingertip insert opening, and "a sheet body attached on the interlabial pad", and it is enough to apply them to any one of them (See FIG. 2). By a similar reason of the above, it is not required to apply the color or the pattern on the rear surface side sheet or whole surface of the sheet body, and the application may be made only the neighborhood of the fingertip insert openings (See FIG. 12).

For a method of applying the different color on the sheet, a method of mixing the material resin of the rear surface side sheet of the sheet body with the coloring agent to apply the color to the rear surface side sheet and the sheet itself, a method of printing a pigment on the rear surface side of the sheet or the sheet body, a method of transferring the mixture of the hot melt adhesive and the pigment on the rear surface side sheet or the sheet body, are eligible.

In this case, the coloring in blue group, red group, green group, yellow group and the like is preferable for manufacturing. Particularly for applying the color on the sheet body, brown and yellowish brown such as resembling the color of skin is more preferable. Thereby the presence of the interlabial pad in wearing comes to be inconspicuous so as to be comfortable for the wearer.

For a method of applying the pattern, for example, at the neighborhood of the fingertip insert opening, in respect of the rear surface side sheet and the sheet body, a method of printing a circular or a triangle, a house mark and the like and a method of pressing the pattern by an emboss process are illustrated.

(7) An interlabial pad according to any one from (1) to (6), wherein the interlabial pad or the absorbent body enclosed in the interlabial pad comprises a folding guide element along said symmetric axis.

According to the interlabial pad of the present invention, in respect of the interlabial pad or the absorbent body contained therein, on the center area of the lateral direction, a folding guide element is provided along the longitudinal direction. Therefore, the wearer slightly draws two fingertips each other which are inserted into openings, the interlabial pad is easily folded along the folding guide element. Further an adequate raising area is formed according to the folding guide element regardless of the folding action of the wearer.

This "folding guide element" may direct the folding position of the interlabial pad so that the folded interlabial pad is easily engaged in pudendal cleft of the wearer and a series of continuous elements or elements spaced from each other are eligible.

(8) An interlabial pad according to (7), wherein the folding guide element is comprised of any of a broken line, a cut line, and a compression line.

In the interlabial pad according to the present invention, a folded guide element is formed by a broken line, a cutting line formed by alternatively arranging broken lines and unbroken lines, or the compressed line.

For a method of constructing the folding guide element by a cutting line, for example, a method of providing the element that the absorbent body is divided in left and right side by a rotary cutter mounted with a straight line-shaped hard blade is eligible. In this case, preferably the length of the broken line portion is in a range from 1 to 5 mm, and an unbroken portion between broken line portions is in a range from 0.3 to 5 mm.

A method of comprising the folding guide element by "compression line", a method of forming the element is so eligible that the interlabial pad or the absorbent body contained in the interlabial pad is treated by an emboss process in a range of the width from 0.5 to 3 mm, a portion to form the folding position is pressed down by a pressure greater than the periphery.

(9) An interlabial pad according to any one from (1) to (6), a long protruding area is provided along the symmetric axis, in using the pad, each fingertip of two fingers of the wearer is respectively inserted into the pair of fingertip insert opening, thereafter the pad is folded at the symmetric axis to be subjected to use in a condition that the long protruding area is projected more.

According to the interlabial pad of the present invention, as described in (1), the raising area is not formed for the first time in using the pad but a long protruding shaped area is preliminarily formed on the pad. Therefore the pad has a shape capable of easily lining along labia regardless of the wearer's handling.

Particularly in the case that the long protruding shaped area is separately provided on the interlabial pad, the volume of protrusion in respect of the interlabial pad comes greater so that the interlabial pad can be inserted certainly into the neighborhood of ostium vaginae which locates at the deep of labia, thereby an efficiency to protect the menstrual blood from leak is improved much.

(10) An interlabial pad according to (9), the long protruding area is formed by bending the symmetric axis.

According to the interlabial pad of the present invention, the long protruding area is formed by folding the interlabial pad. Therefore, in a case of holding the interlabial pad or a sheet body by fingertips which are inserted in fingertip insert openings, the interlabial pad is guided and deformed certainly into a mountain folded shape. As a result, the interlabial pad has a form easily lining along pudendal cleft.

In the case that the sheet body is attached on the interlabial pad, the sheet body forms the fingertip insert opening and further has an effect of regulating a spread of the long protruding area formed by folding the interlabial pad.

(11) An interlabial pad according to any one from (1) to (10), the interlabial pad is used together with a sanitary napkin.

According to the interlabial pad of the present invention, the pad can be used together with a sanitary napkin. Thereby in case that the interlabial pad receives a volume of body fluid exceeding its capacity, it can certainly prevent from the underwear getting dirty by a leak of the body fluid.

Since sanitary napkins are laminated with each other only around ostium vaginae, unlike the use of laminated napkins, it can be avoided to feel bad wear feeling such as stiffness, to be noticeable from the outside of the garment, or to cause a rash or a stuffiness by laminating napkins around ostium vaginae and toward portions not to be necessary treated by the pad. Further only the pad can be altered without changing the napkin, thereby the person is prevented from carrying always a noticeable size of napkin.

(12) An interlabial pad according to any one from (1) to (11), the interlabial pad is an interlabial pad for incontinence of urine.

According to the interlabial pad of the present invention, the pad can be used for incontinence absorbing pad. That is, ostium vaginae where the menstrual blood is discharged and a urethral meatus where urine is discharged locate between labia, and the interlabial pad of the present invention to be used between labia can absorb urine also.

As described hereinbefore, the pad of the present invention can absorb urine around labia, especially around the urethral meatus, and is useful as the absorbent pad for incontinence of urine, especially for a light incontinence of urine.

(13) An interlabial pad according to any one from (1) to (11), the interlabial pad is an interlabial pad for absorbing vaginal discharge In accordance with the present invention, the interlabial pad can be used for the pad of absorbing the vaginal discharge. That is, the interlabial pad is used between labia and can absorb the excretion other than the menstrual blood from ostium vaginae for the use therefore (for absorbing the vaginal discharge).

As described above, the pad can absorb the vaginal discharge in order to decrease the discomfort for the person, and is useful for the wearer who is not menstruating.

(14) A wrapping body comprising an interlabial pad according to any one from (1) to (13) and a wrapping container to contain the interlabial pad, wherein said interlabial pad is folded in a mountain folded shape toward a body side along said symmetric axis and is contained in said wrapping container.

According to a wrapping body for the interlabial pad of the present invention, the fingertip insert opening is positioned at the neighborhood of the unseal portion of the wrapping container. Therefore, the wearer breaks a seal of the wrapping container and can see the fingertip insert opening by eyes to insert the fingertip rapidly into the opening so as to hold the interlabial pad.

(15) A wrapping body according to (12) comprising the interlabial pad according to any one from (1) to (13) and a wrapping container to contain the interlabial pad, wherein the interlabial pad is folded in a mountain folded shape toward a body side along the symmetric axis and is contained in the wrapping container.

According to the wrapping body for the interlabial pad of the present invention, the pad is preliminarily folded at the center of the lateral direction along the longitudinal direction and is contained. Thereby the wearer can pick the wrapping container by one hand and can take out the interlabial pad by the other hand, and the trouble of dropping the pad from the wrapping body can be prevented previously. Further the operation of folding the pad in mountain folded shape has been made during the stage of containing the pad in the wrapping container, and the mountain folded state can be easily maintained by a habit of folding on the folding portion. Thereby the operation of wearing the pad comes more easily.

BEST MODE OF CARRYING OUT THE INVENTION

The preferable embodiment of the interlabial pad in accordance with the present invention will be described with reference to accompanied drawings.

[Structure of Interlabial pad with Sheet Body]

Figure 1:
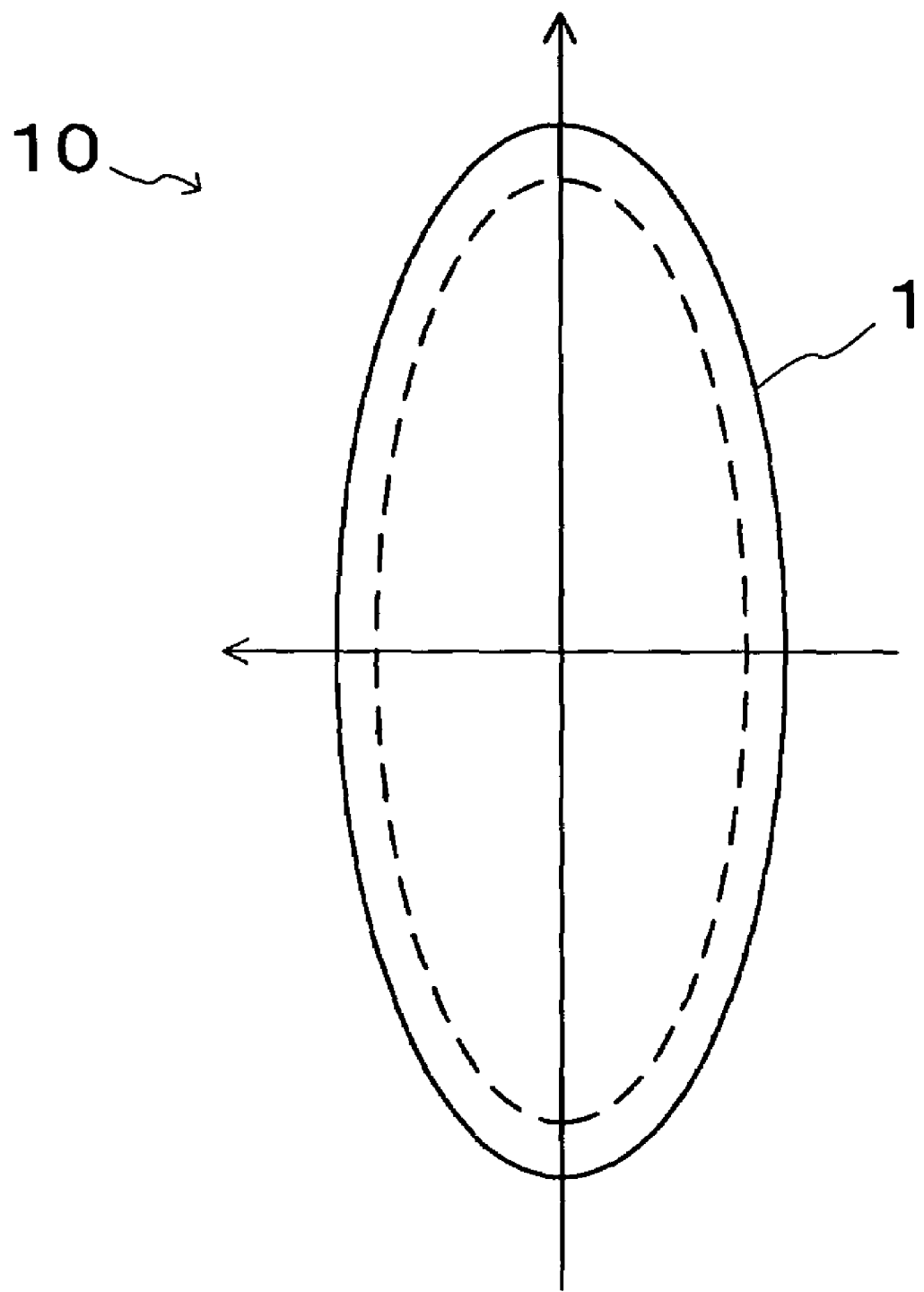
FIG. 1 is a view which shows the body side of the interlabial pad provided with the sheet of the embodiment of the present invention.
Figure 2:
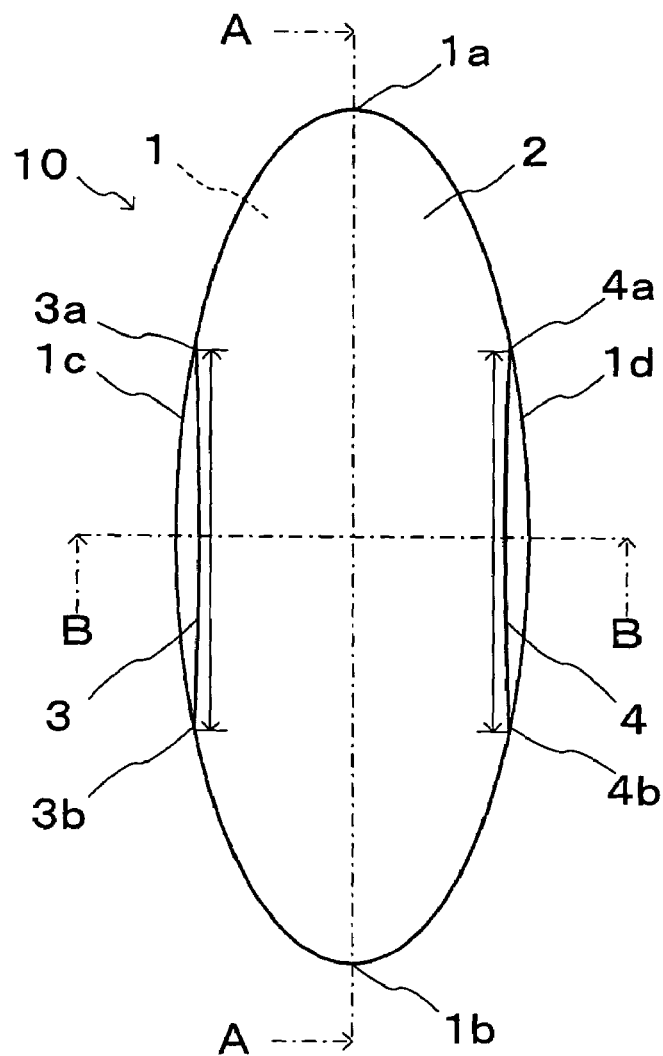
FIG. 2 is a view which shows anti-(reverse) body side of the interlabial pad provided with the sheet body in accordance with the embodiment of the present invention.
Figure 3:
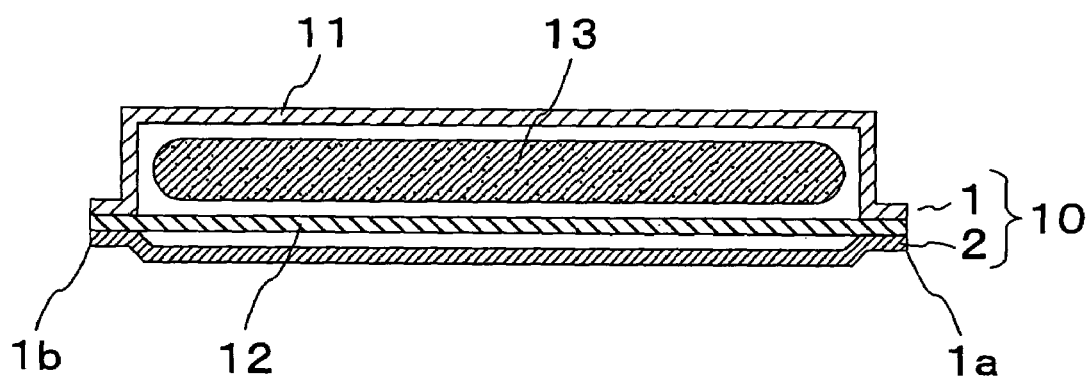
FIG. 3 is a cross section view shown along line A-A of FIG. 2.
Figure 4:
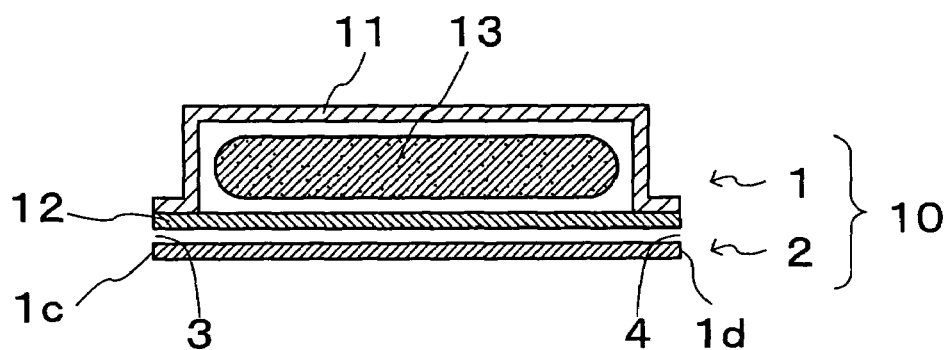
FIGS. 4A-B illustrate a cross section view shown along line B-B of FIG. 2.
Figure 4:
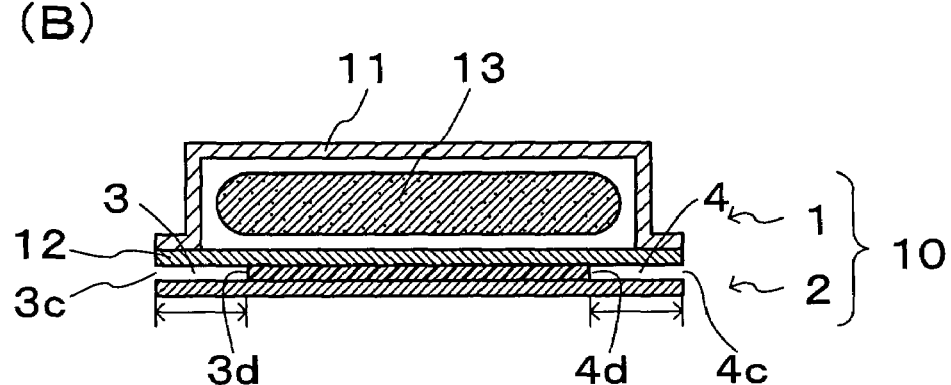
Figure 5:
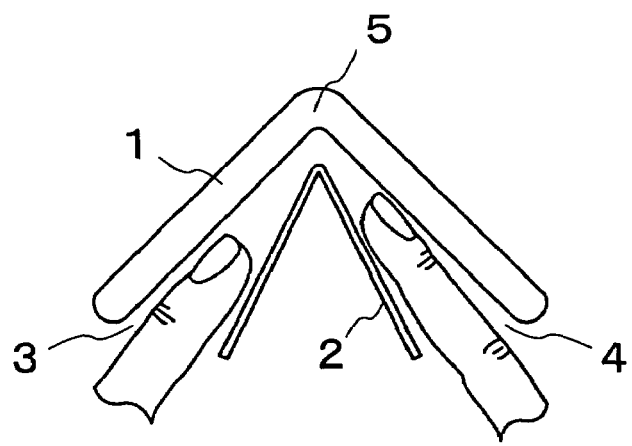
FIG. 5 is an explanation view which shows a condition of inserting the finger into the fingertip insert opening of the interlabial pad provided with the sheet body in accordance with the embodiment of the present invention.

FIG. 1 illustrates a body side of an interlabial pad 10 provided with a sheet body, FIG. 2 illustrates the reverse body side of the pad 10 with the sheet body, FIG. 3 is a cross section view along A-A line of FIG. 2, FIG. 4 is a cross section view along B-B line of FIG. 2 and FIG. 5 is an explanation view of inserting two fingers into the finger insertion opening 3, 4.

As shown in FIG. 1, the interlabial pad 1 is a substantially oblong shape having left and right side end portions and front and rear side end portions. The outline shape of the interlabial pad 1 can be formed in various shapes such as a long oval shape as the embodiment of the present invention, or a rectangular shape, a sandglass shape and the like, which can be held by labia.

As shown in FIG. 2, at the reverse body side of the interlabial pad 1, the sheet body 2 is attached. As shown in FIG. 3, the sheet body 2 is connected in respect of both end portions 1a, 1b and of the neighborhood in the vertical direction of the pad 1 is designed in disconnected with a central areas 1c, 1d of both left and right side edge portions of the horizontal direction of the pad as shown in FIG. 4 (A). Further apparently shown in FIG. 2, the finger insertion openings 3, 4 are formed on the disconnecting areas.

The fingertip insert openings 3, 4 have a size sufficient to insert the wearer's finger smoothly, specifically the width size of the opening (a size of the length from one side end portion 3a to the other end portion 3b) and the width size of the opening 4 (a size of the length from one end portion 4a to the other end portion 4b) are set from 25 to 35 mm respectively.

Further in this embodiment, openings 3, 4 connect with each other to form a tunnel, as shown in FIG. 4 (B), the interlabial pad 1 and the sheet body 2 are adhered on a center of the lateral direction along the vertical axis, fingertip insert openings 3, 4 may be formed in an individual clearance respectively. In this case, preferably each depth size of the fingertip insert opening 3, 4 (a length size from an opening portion 3c to an end portion 3d), (a length size from an opening portion 4c to an end portion 4d), is more than 15 mm respectively.

For connecting the sheet body 2 with opposite body side surface of the interlabial pad 1 can be achieved by a conventional method such as ultrasonic wave sealing, a heat sealing and the like.

In the embodiment of the present invention, as shown in FIG. 2, the vertical directing size of the sheet body 2 is same as the interlabial pad 1, however the size of the horizontal width of the sheet body 2 is slightly shorter than the interlabial pad 1. Thereby the interlabial pad 10 with the sheet body is observed from the opposite side to the body side, a part of the opposite side to the body side surface of the pad 1 is exposed, and the wearer can confirm fingertip insert openings 3, 4 without reversing the interlabial pad 10 with the sheet body. In addition thereto, the opposite side to the body side surface of the pad 1 is colored in a different color of the sheet body 2, thereby the wearer can confirm fingertip insert openings 3, 4 more easily.

As shown in FIG. 5, the wearer inserts the thumb from the fingertip insert opening 3 and inserts the forefinger into the fingertip insert opening 4 to hold the sheet body 2 by two fingers. Since the interlabial pad 1 and the sheet body 2 are adhered on the periphery edge portions except of openings 3, 4, the sheet body 2 is only picked, accordingly the interlabial pad 1 is folded in a mount holding shaped.

As shown in FIG. 3, FIG. 4(A), (B), the structure of the interlabial pad 1 has an absorbent body 13 held between water permeable surface side sheet 11 and non-water permeable rear surface side sheet 12 and the outer surface side sheet 11 and the rear surface side sheet 12 contacted and adhered with each other on the peripheral portion of the absorbent body 13. In this case, for adhering the outer surface side 11 and the rear surface side sheet 12, the sheet body 2 is simultaneously adhered. The connecting may be achieved by a single heat sealing or together with a hot melt-typed adhesive.

The structure of the interlabial pad 1 is not limited to the example described hereinbefore such as adhered type, an enclosing type may be eligible that non water permeable material is disposed under the absorbent body and whole thereof is covered by water permeable sheet.

[Method of Using Pad]

Figure 6:
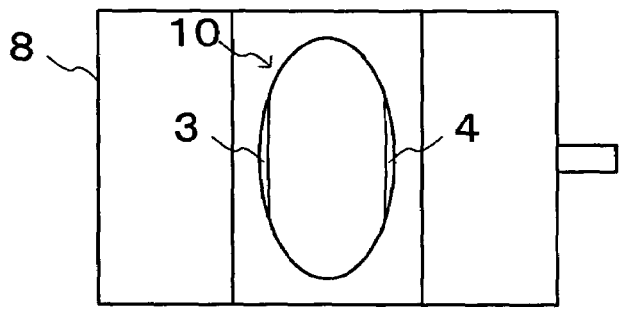
FIGS. 6(A) to 6(D) are diagram views of the process by the time of taking out the interlabial pad with the sheet body out from the wrapping container.
Figure 6:
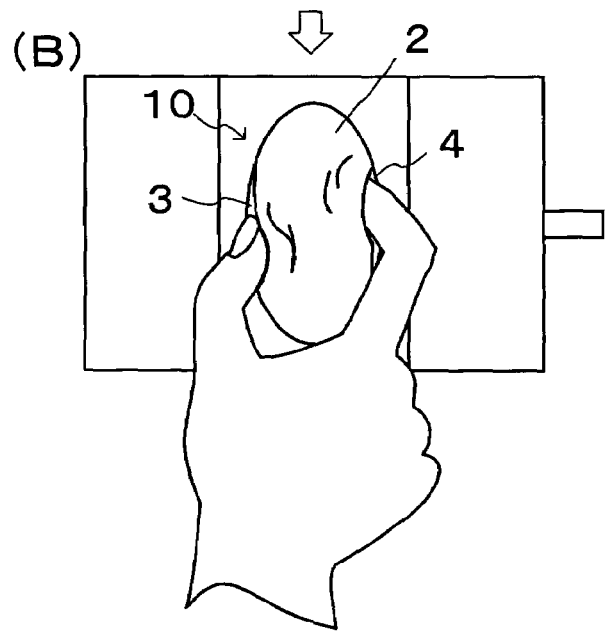
Figure 6:
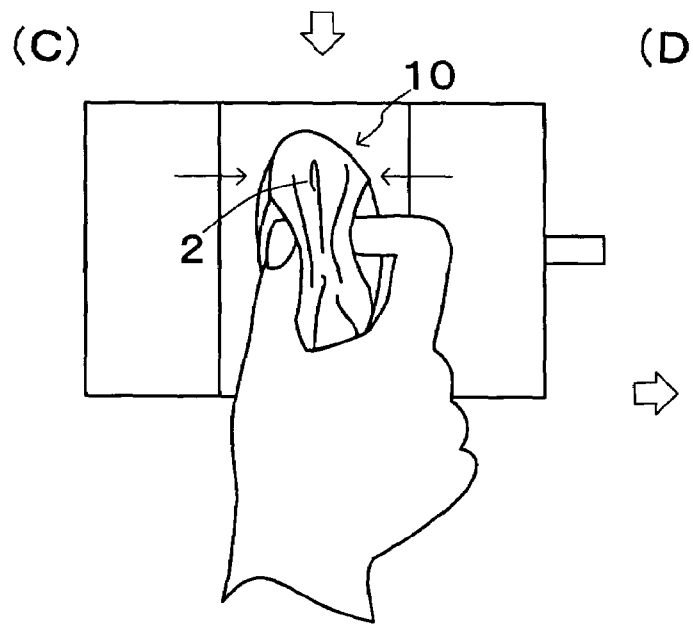
Figure 6:
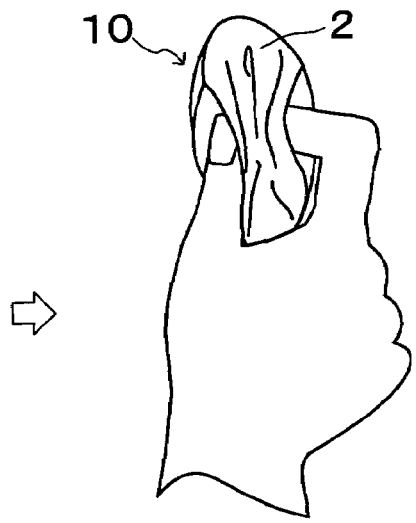

A method of using the pad 10 with the sheet body will be described hereinbelow. FIG. 6 illustrates a diagram of the process of taking out the pad 10 from the wrapping container formed by a wrapping sheet 8, FIG. 7 illustrates the pad of FIG. 6(D) which is observed from the body side, and FIG. 8 illustrates a condition of wearing the pad 10 with the sheet body into labia.

As shown in FIG. 6(A), the wrapping container comprising the wrapping sheet 8 is broken to expose the interlabial pad 10 with the sheet body. In this case, the pad 10 with the sheet body is contained in the wrapping container in contacting the body side surface with the wrapping sheet 8. Thereby the wearer opening the container can see the interlabial pad 10 with the sheet body from opposite body side, and can confirm the fingertip insert openings 3, 4 soon.

Further as shown in FIG. 6 (B), the fingertip is inserted into the opening 3 and a forefinger is inserted into the fingertip insert opening 4. As shown in FIG. 6(C), the wearer holds the sheet body 2 by these two fingers to pull up the interlabial pad with the sheet body, thereafter holds it at fingertips as shown in FIG. 6(D).

Figure 7:
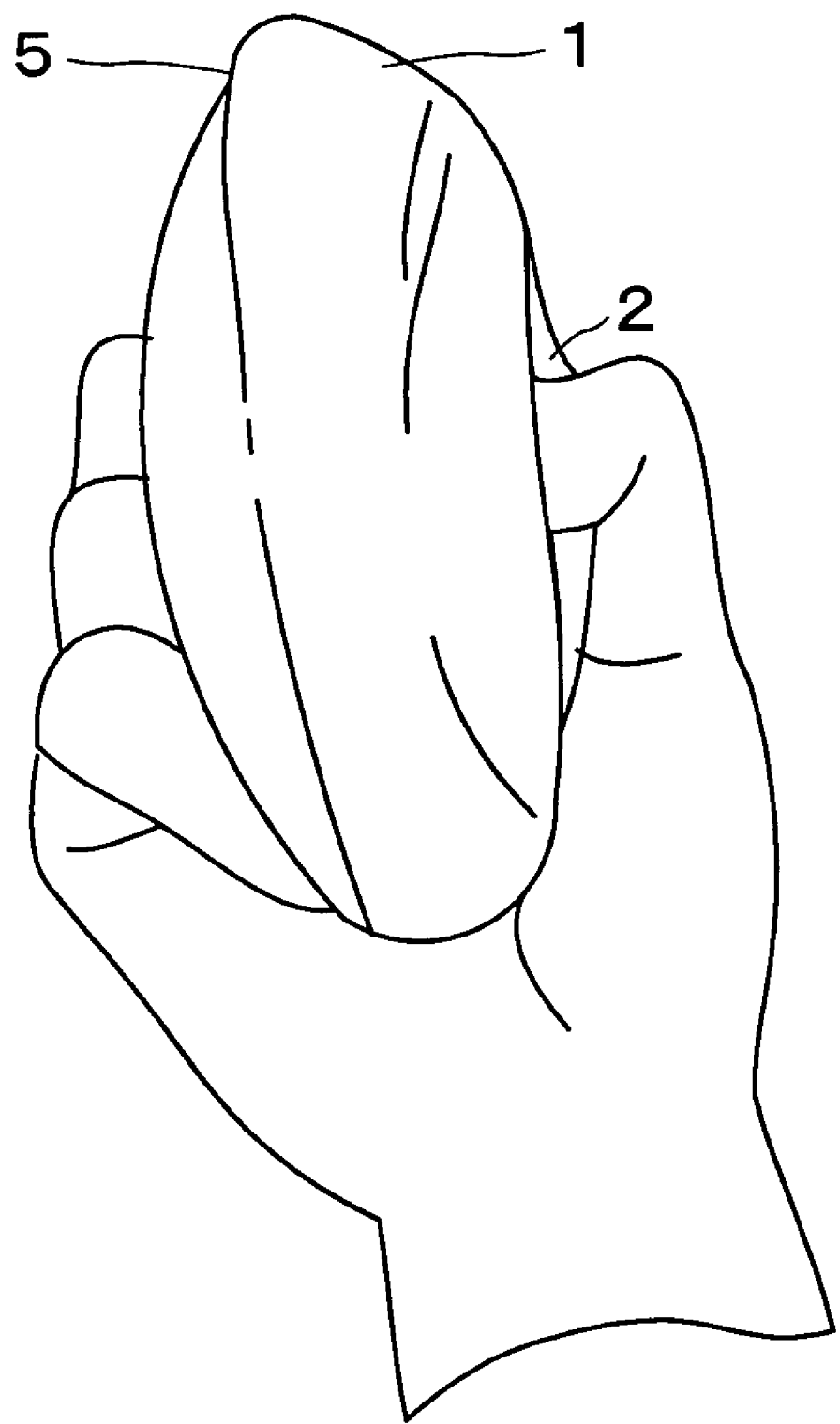
FIG. 7 is a view which shows the interlabial pad provided with the sheet body shown in FIG. 6(D), observed from the body side.
Figure 8:
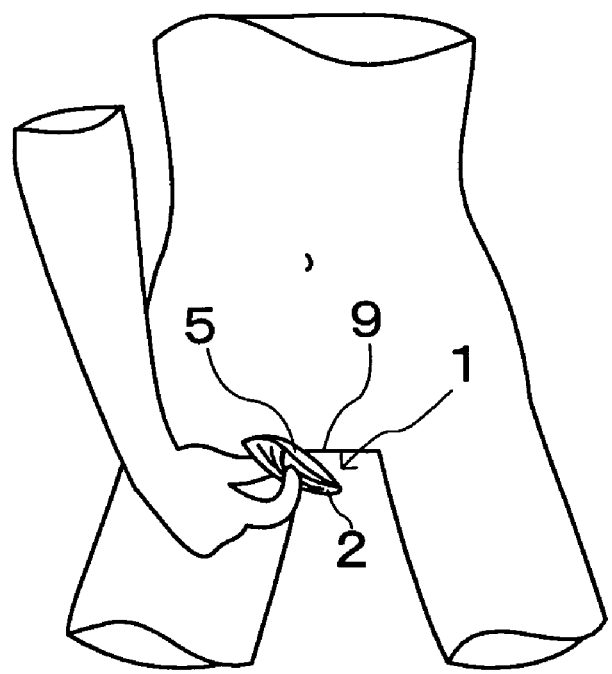
FIG. 8 is a view which shows a condition of wearing the interlabial pad with the sheet body into the labia.

As shown in FIG. 7, by picking the sheet body 2, the interlabial pad 10 with the sheet body is folded in a vertical direction accordingly, the center portion is raised to the body side to form a raising area 5. As shown in FIG. 8, the wearer keep only a condition of holding the sheet body 2 to keep the folded state of the pad 1 till the pad is attached to labia 9, thereby the pad can be attached to insert the raising area 5 into labia.

[Other Embodiments of Interlabial pad]

Figure 9:
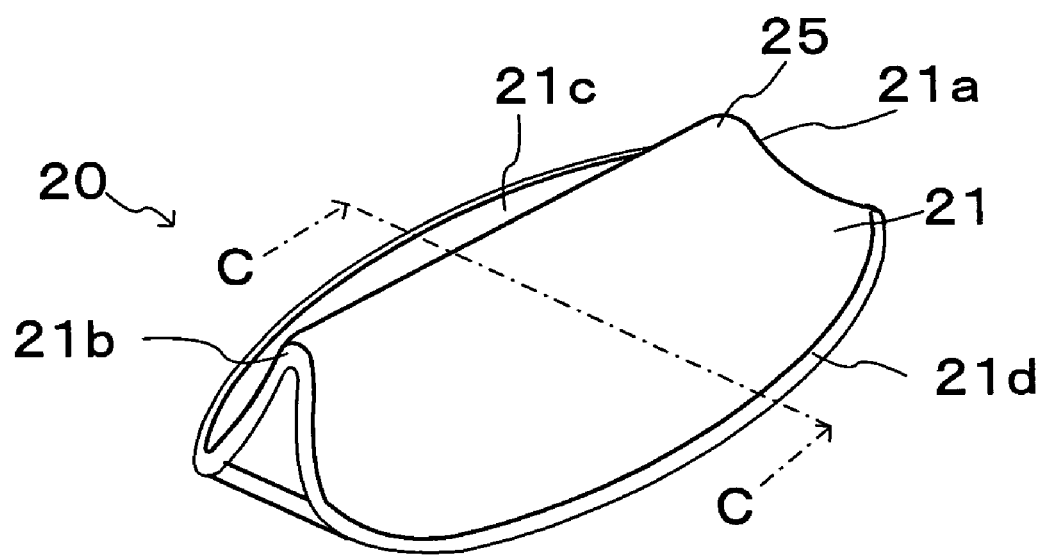
FIG. 9 is a perspective view which shows the interlabial pad provided with the sheet body, having a long protruding area on the body side surface.
Figure 10:
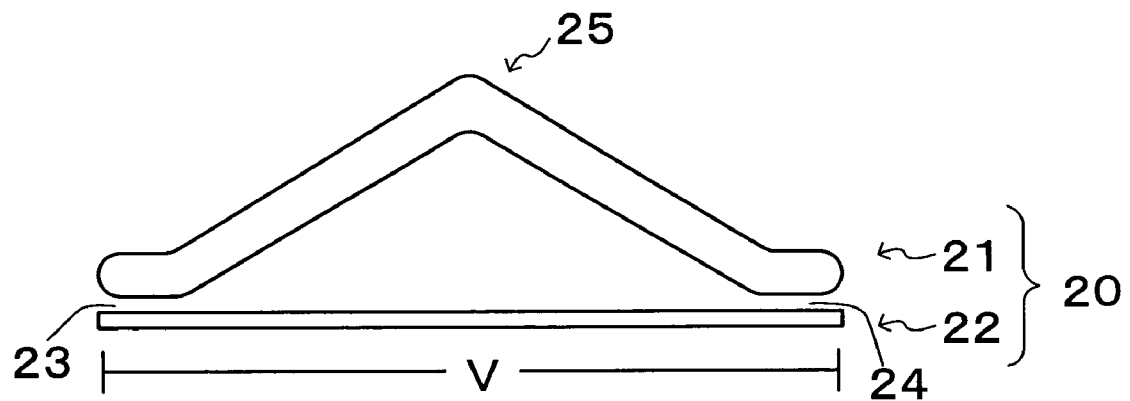
FIG. 10 is a cross section view along C-C line of FIG. 9.
Figure 11:
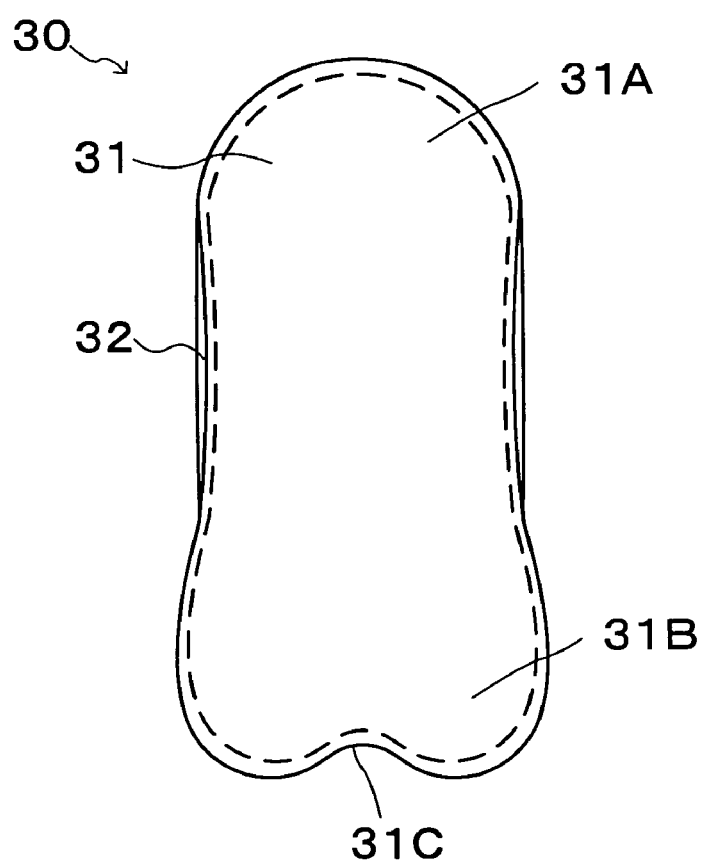
FIG. 11 is a view which shows the body side surface of the interlabial pad provided with an oblong heart-shaped sheet body.
Figure 12:
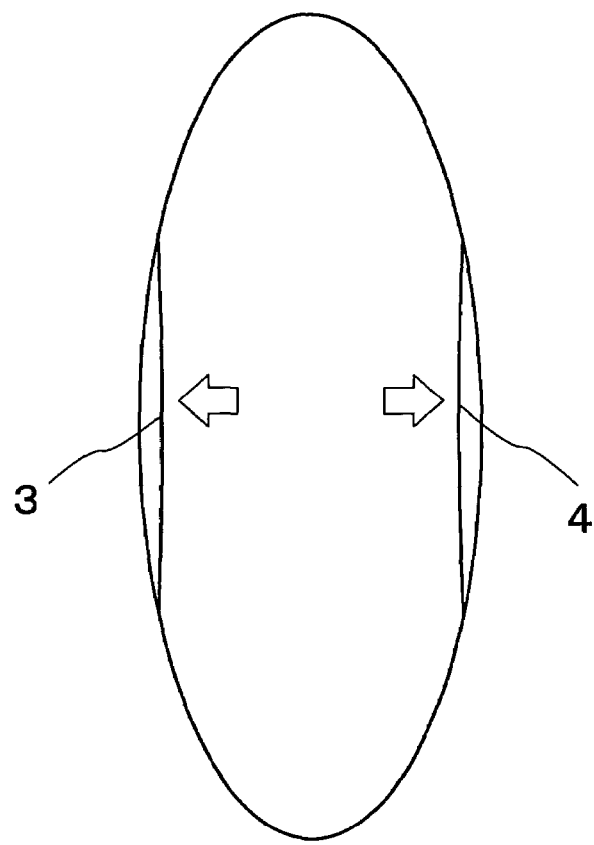
FIGS. 12A-B illustrate views which shows opposite body side surface of the interlabial pad provided with the oblong heart-shaped sheet body.
Figure 12:
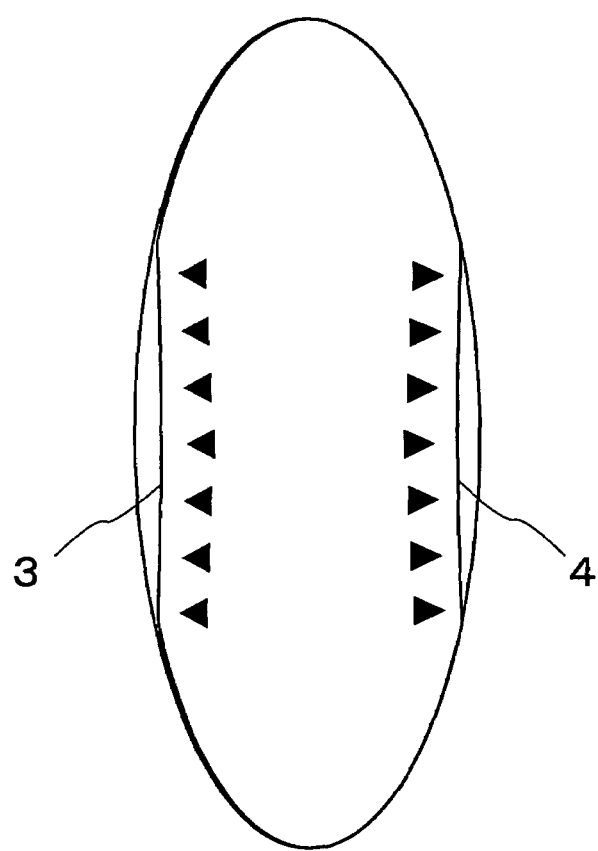

Other embodiments of the interlabial pad will be described hereinafter. FIG. 9 illustrates a perspective view of the interlabial pad 20 with the sheet body which includes a long protruding area 25 on the body side surface of the pad 21, FIG. 10 is a cross-section view along C-C of FIG. 9. FIG. 11 illustrates the body side surface of the interlabial pad 30 with the oblong heart-shaped sheet body, FIG. 12 illustrates the interlabial pad 10 with the sheet body provided the sheet body 2 with a pattern.

As shown in FIG. 9, the pad 21 is folded toward the body side with the substantial center of the lateral direction being a top and the oblong protruding area 25 is formed on the folded portion. In elongated area connecting to left and right side of the long protruding area 25, the sheet body 22 is attached. The sheet body 22 is connected on the neighborhood of both end edges 21a, 21b of the interlabial pad, and has disconnecting area on side edges 21c, 21d. Further on this disconnecting area, as shown in FIG. 1, the fingertip insert openings 23, 24 are formed.

For a function of regulating an extension of the long protruding area 25, regardless of whether or not the wearer operates to fold the pad, in the sheet body 22, the adequate form of long protruding area 25 is kept till the pad is worn.

As shown in FIG. 11, the interlabial pad 31 is formed in an oblong heart shaped, the sheet body 32 is attached thereon and the interlabial pad 30 with the sheet body may be formed. In the case of forming the pad 31 in such shape, the forward area 31A locating the forward of the wearer comes narrow in wearing the pad and the contacting area of the femoral region inside and the pad 31 is decreased. While the front area is widened, in the case that the leg of the wearer moves violently, due to the friction which is caused by scrapping the inside of the femoral region with the pad side portion, there is a fear of dropping off the interlabial pad. In this point, the pad 31 is formed so that the forward area 31A to be narrow, thereby the friction force on the pad 31, caused by moving legs of the wearer is decreased and it comes to be difficult to occur of shifting the wearing position of the pad 31.

Further the rearward area 31B of the pad 31 is formed to be wide, thereby the rearward area 31B having a wide outer surface area can receive the menstrual blood to absorb it in case of much menstrual blood, particularly in the case of the menstrual blood is suddenly discharged from ostium vaginae.

Furthermore, the rearward area 31B includes a groove portion 31C on a center of the rear end portion, and the vertical size of the pad 31 is long. However, it is formed to easily fit in the breech. In this point, in the case that the rearward end center portion of the pad is not formed to be concave shaped, for example, the rearward end portion is U-shaped same as the front end portion, the vertical size of the pad 31 is elongated, the center of the rearward end portion comes to be sticking out of the groove of the breech. Resultantly the rear end center portion contacts with the underwear to cause a shift of the wearing position for the interlabial pad, the rear end center portion cannot contact with the groove of the breech to cause a clearance through which the menstrual blood leaks. In this point, in the embodiment of the present invention, at the presence of the groove portion 31C, the end of the rearward area 31B is designed to easily fit with the shape of the wearer's breech, the absorbing efficiency of the pad 31 can be increased in keeping the sealing efficiency of the pad and the wearer's breech.

In the interlabial pad 10 as shown in FIG. 2, the rear surface side sheet 12 is colored, thereby the wearer can confirm easily the openings 3, 4, while the rear surface side sheet 12 is not colored and the sheet body 2 is applied with a coloring or a pattern, thereby the wearer can confirm easily openings 3, 4. For example, as shown in FIG. 12 (A), an arrow is printed to indicate openings 3, 4, and as shown in FIG. 12(B), the sheet body 12 can be printed a triangle pattern to indicate opening 3, 4.

[Wrapping Condition]

The wrapping condition of the interlabial pad will be described.

Figure 13:
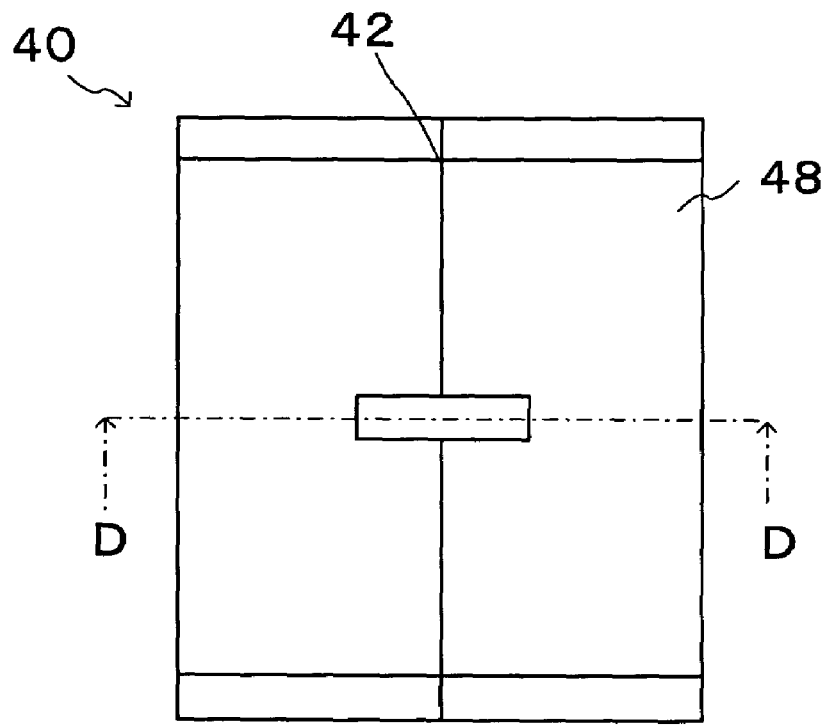
FIG. 13 is a view which shows the interlabial pad with the sheet body which is provided with a pattern.
Figure 14:
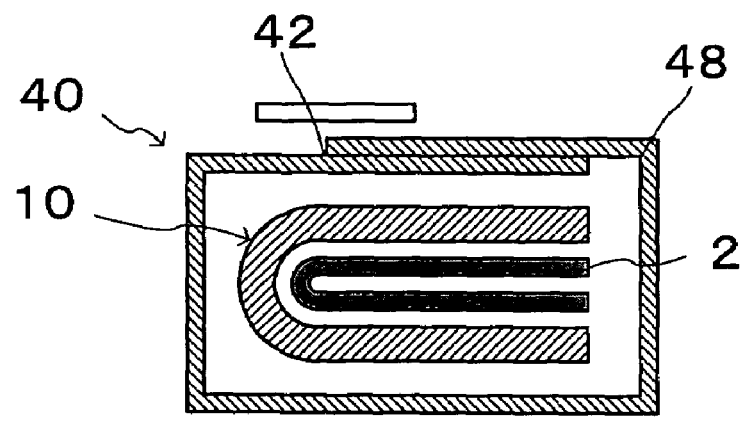
FIG. 14 is a cross section view along D-D line of FIG. 13.
Figure 15:
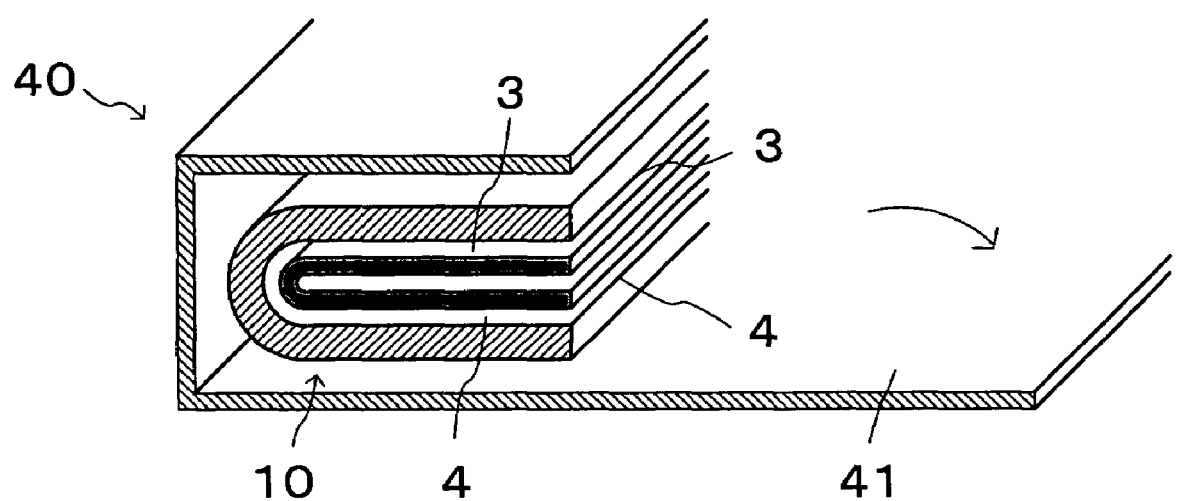
FIG. 15 is a perspective view of a condition that the wrapping container formed by the wrapping sheet is broken the seal.
Figure 16:
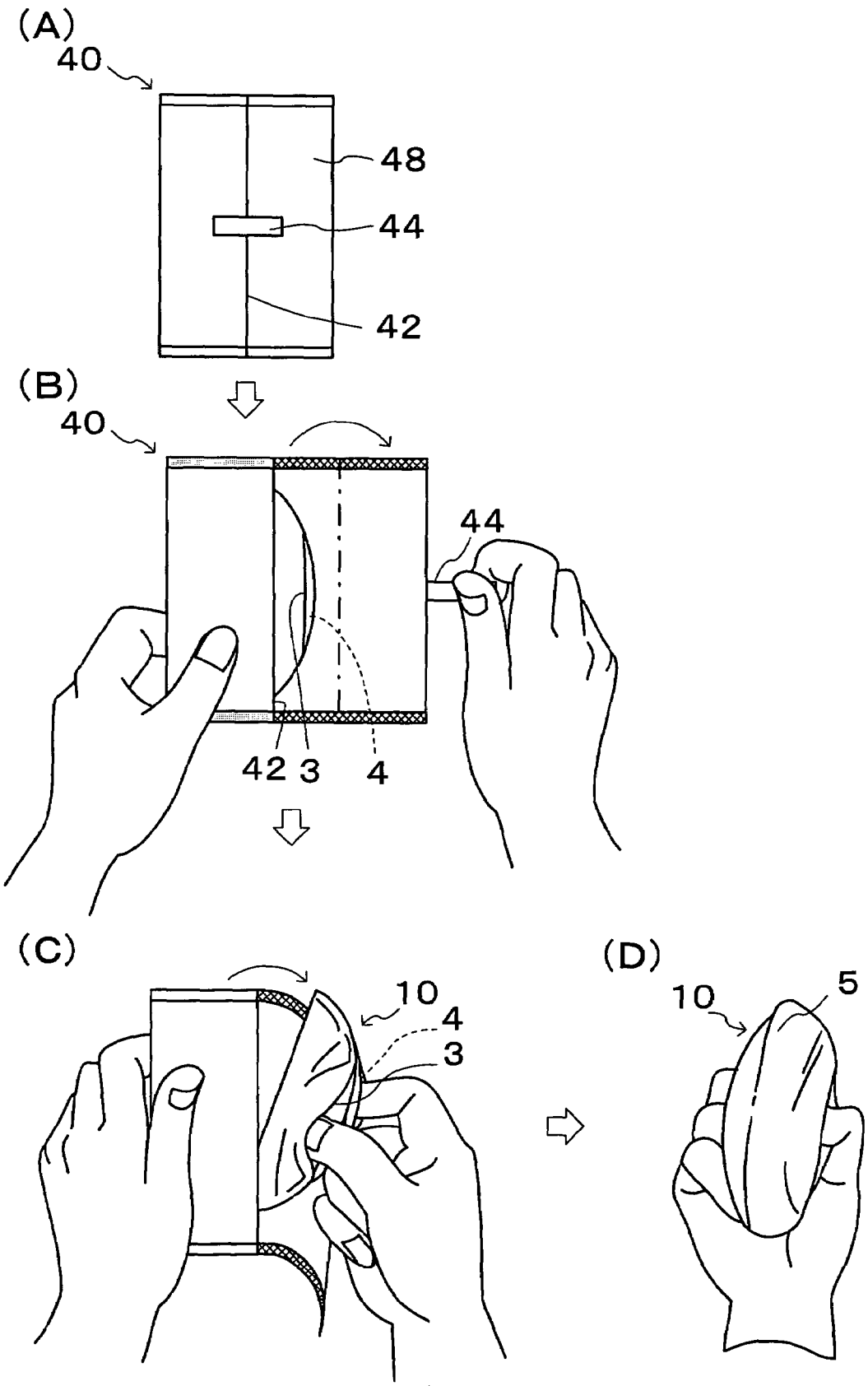
FIGS. 16(A) to (D) are diagram views of the process of breaking the seal of the wrapping container to take out the interlabial pad with the sheet body.

FIG. 13 illustrates a wrapping body 40 containing interlabial pad 10 with a sheet body in a wrapping sheet 48, FIG. 14 is a cross-section view along D-D of FIG. 13, FIG. 15 is a cross-section view illustrating a condition of breaking the seal of the wrapping container 41, FIG. 16 is a diagram view of the process for taking out the pad 10 by breaking the seal of the wrapping container 41.

As shown in FIG. 13, the wrapping container is formed by connecting upper and lower edges of the wrapping sheet 48 with each other in preventing from laminating with the pad (not shown). The breaking portion 42 of the wrapping container is provided to open in a horizontal direction and the connection of upper and lower ends is adjusted to break off to take out the pad. The method of the adjustment are, for example, a conventional technique such as a press by a heat emboss and a confounding by an emboss.

As shown in FIG. 14, the interlabial pad 10 with the sheet body is contained in a folded state so that the sheet body 2 is place in an inside thereof centering with a vertical axis. Therefore the body side of the pad 2 is contacted with the wrapping sheet 48.

As shown in FIG. 15, the breaking direction of the wrapping container 41 is set to the opposite direction of the pad 10 with the sheet body which is folded, as both facing to the same direction, the folded side of the pad cannot be observed in breaking the seal of the container 41. Thereby the wearer need not to change the direction of the pad with the sheet body which is taken out, can observe the opening 3, 4 for inserting the fingertip simultaneously with the breaking and can insert it into the opening 3, 4 rapidly.

In taking out the pad with the sheet body from the wrapping body 40, at first, as shown in FIG. 16 (A), the wrapping container 41 is set so that the unseal portion 42 and a sealing tape 44 come on the upper surface. As shown in FIG. 16 (B), the wearer catch the wrapping body 40 by another hand than a dominant hand, and the sealing tape 44 is hold and pulled by her fingertip of the dominant hand to break a seal of the breaking portion 42. Thereby the fingertip insert opening 3, 4 are exposed. Thereafter as shown in FIG.16(c), the wearer inserts the thumb into the opening 3 and the forefinger into the opening 4 to take out the interlabial pad with the sheet body. Thereby as shown in FIG. 16 (D), the wearer can keep the pad 10 in a state of forming the raised area 5.

[Outer Size of Interlabial pad]

The outer size of the interlabial pad will be described hereinbelow.

In consideration of closing possibility of labia, a vertical and a horizontal size of interlabial pad is designed in a range of being engaged in labia and of being held by a force of labia of itself. More specifically the vertical size is in a range from 60 to 150 mm, more preferably from 80 to 120 mm, a size of an appearance in a lateral direction of the interlabial pad is preferably in a range from 10 to 60 mm, more preferably from 20 to 40 mm. If the size of the lateral direction is longer than 60 mm, due to the friction which is caused by scrapping the area of the pad out of labia with the inside of the femoral region, there is a fear of dropping off the interlabial pad because of the friction can overcome the holding force of labia. While the length thereof is less than 10 mm, the pad area comes to be less within labia, and the contacting area with the inner surface of labia is decreased to cause a fear of dropping off the pad.

Figure 17:
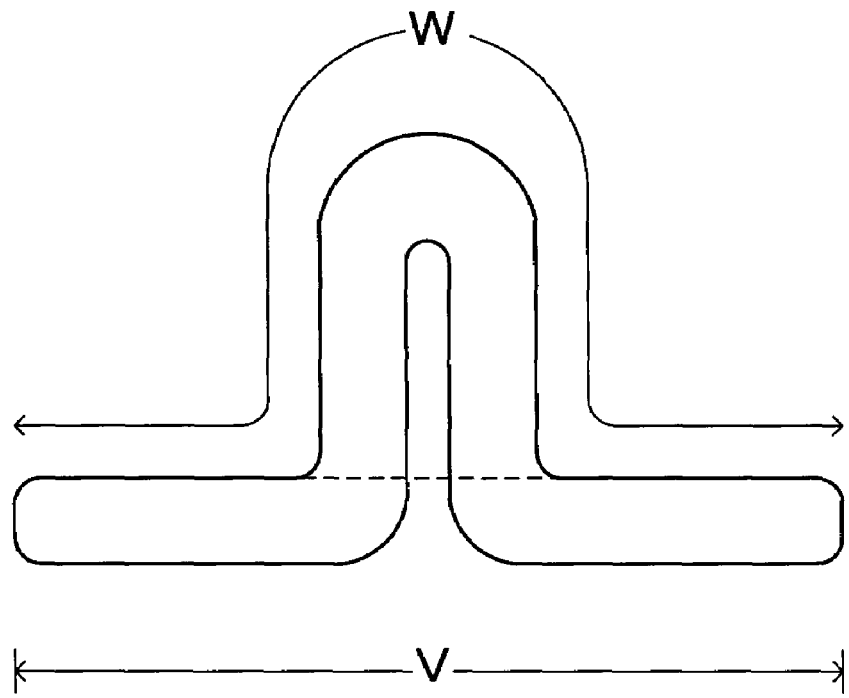
FIG. 17 is an explanation view for describing a size of the length of the lateral direction of the interlabial pad.
Figure 18:
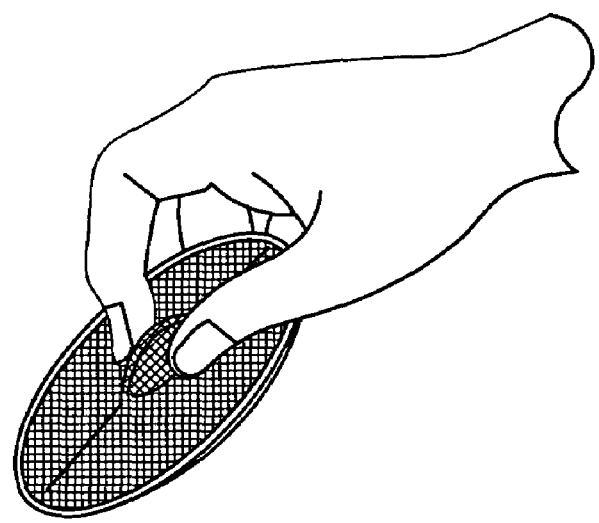
FIG. 18 is a view which shows the condition to use the conventional pad having a projection on the reverse body side surface of the interlabial pad.

The word "in appearance" means that the length is the minimum distance between two points (corresponding to V in FIG. 17). Since in the production process, there is a case that the distance tracing the uneven form, that is, the distance between two points of the pad having the uneven shape extended in a flat condition, is treated as a substantial distance (corresponding to W in FIG. 17), the distance is defined very carefully.

A size of the absorbent body contained in the interlabial pad is same as the size of the pad, or in consideration of the strength of the peripheral edge portion, is shortened by 2 to 10 mm with spaces from the outline. The thickness of the absorbent body is preferably in a range from 2 to 10 mm, more preferably from 3 to 6 mm for providing a good feeling not to damage the wear feeling.

[Materials Comprising Interlabial pad]

<Permeable Sheet>

Preferably the permeable sheet disposed on the body side of the pad is liquid permeable and non-stimulate materials are used. For example a material is a single nonwoven fabric which is obtained by a manufacturing method such as a melt blown, a spun bond, a point bond, a through air, a needle punch, wetting spun lace or a foam film, or a combination of them.

It is also preferable to use an individual or a mixed sheet-typed fiber which is selected from a single fiber or combined fiber having a sheath-core structure comprising of a rayon, an acetate, a cotton or a pulp such as a natural fiber, or a synthetic resin, from a hydrophilic treated synthetic fiber and the like.

Among the materials, considering the liquid mobility from the inner face of the labia, chemical stimulation by an activator, and adhesion with the inner wall of the labia, it is preferable to laminate rayon with 1.1 to 4.4 dtex fineness and 7 to 51 mm fiber length by 40 to 80% of a total specific weight per unit area on the body face side, and to laminate a mixture of rayon with 1.1 to 4.4 dtex fineness and 7 to 51 mm fiber length by 14 to 42% of a total specific weight per unit area and PET with 1.1 to 4.4 dtex fineness and 7 to 51 mm fiber length by 6 to 18% of a total specific weight per unit area on the garment face side. After laminating them so that the total specific weight per unit area of the two layers becomes 20 to 60 g/m$^2$, the fibers are entangled by water flow interlacing treatment and then dried to prepare spun lace nonwoven fabric with the thickness of 0.13 to 0.50 mm. The spun lace nonwoven prepared as described is preferable. At this time, by mixing PET on the garment face side, bulkiness can be easily maintained even if the water permeable sheet becomes wet. Therefore, adhesion to the inner wall of the labia can be maintained <Absorbent body>

A single and a compound mixing of pulp, chemical pulp, rayon, acetate, a natural cotton, super absorbent polymer, fiber-typed super absorbent polymer and a synthetic fiber are eligible for materials. an absorbent body contained in the interlabial pad. A mixture combined as desired is formed in a sheet by a conventional technique such as a press by an emboss process or a confounding by a needling and can be adequately adjusted by adjusting, laminating or folding its bulkiness if necessary.

Sheet-shaped materials may be used in a sheet-typed or a particle-typed and is not limited to a way of using.

It is preferable for the absorbent body, although any material can be used as long as it is capable of absorbing and holding liquid (body liquid), to be bulky, hard-to-be deformed, less chemically stimulant, and highly flexible to fit into the labia. Specifically, a nonwoven sheet in which, 50 to 150 g/m$^2$ of pulp selected from the range of the fiber length of 1 to 10 mm is laminated on the garment face side and, on the body face side, 150 to 250 g/m$^2$ of a mixture obtained by mixing 60 to 90% of rayon with 1.1 to 4.4 dtex fineness and 20 to 51 mm fiber length with 40 to 10% of natural cotton by this mixing ratio is laminated, which then to be formed into a sheet by dotted embossing to have 2 to 10 mm bulkiness, and more preferable to have 3 to 5 mm bulkiness. Thereby, liquid can be easily transferred from the body face side to the garment face side resulting in the improvement of the absorbing and holding capacity. Furthermore, by providing a mesh spun lace nonwoven fabric of rayon with 1.1 to 4.4 dtex fineness and 25 to 51 mm fiber length by a specific weight per unit area of 15 to 40 g/m$^2$, the liquid transferred from the body face side can be diffused by the mesh spun lace to be induced to almost all over the region of the pulp layer. Therefore, more liquid can be effectively absorbed.

<Non-permeable sheet>

As a non-water permeability material used for interlabial pad, such material can be used that can prevent the menstrual blood, which is kept in the absorbent body, from leaking out of the interlabial pad. Furthermore the pad can be comprised of water vapor permeability material, thereby in wearing the pad, the sweat and the discomfort can be decreased. For these materials, for example, a sheet-typed film laminated synthetic resin, a porous film comprised that a synthetic resin is filled with inorganic filler and provided with an extension treatment, a laminate film compound of a paper or nonwoven fabric are eligible, further a porous liquid sheet obtained by forming a capillary having 10 to 30% rate of the hole area and a pore size of 0.1 to 0.6 mm toward the absorbent body is eligible.

More concrete example of applying non-water permeability materials, a film mainly of a low density polyethylene (LDPE) is eligible which is obtained from a range of a density 0.900 to 0.025 g/cm3, in amount from 15 to 30 g/m² by a specific weight per unit, based on the total mass per unit area of the composition. The flexibility not to hurt a fixing feeling is considered. More preferably, during the pad applied between labia, non-water permeability sheets are contacted with each other, with the pad which is used together or with the underwear to decrease a fear of dropping the interlabial pad from the labia due to the high friction, the film is treated an embossing process and the convex upheaval portion is disposed, thereby it may decrease a ratio contact by less friction drag.

<Connecting Method of Sheet Body on Opposite Side Face to the Body Side Face of Interlabial Pad>

The sheet body is fixed by the method of pressure sensitive hot melt adhesive, heat sensitive hot melt adhesive, heat seal, ultra sonic seal and the like. The application of the adhesive can be selected from, for example, a surface-shaped, a line-shaped, a spiral-shaped, a dot-shaped and the like.

<Sheet Body>

A material used for the sheet body is selected in consideration of having an enough strength against a damage by the inserted finger, preferably it can be selected individually from one laminated sheet-typed nonwoven fabric, an elastic and expand nonwoven fabric, a film, a foam film, an elastic and expand film, a foam sheet, a tissue paper and the like, singly or in combinations thereof.

Preferably material is selected from which has horizontal directing breaking strength of 0.6N/25 mm, more preferable of 0.6 to 2.5N/25 mm in consideration of a toughness. As embodied, a film mainly of low density polyethylene having a density of 0.915 and a thickness is adjusted from 15 to 30µ is eligible, more preferably a foam film in capable of easily pulling out the finger from the opening and mainly of LDPE resin having a capillary and a density of 0.920, bulkiness of 0.3 to 1.0 mm, a perforation rate from 15 to 60% and a opening diameter from 0.3 to 1.5 mm.

[Structure of the Interlabial Pad Provided with Biodegradability, Water Dispersibility and Water Solubility]

Preferably the interlabial pad is comprised of a biodegradable material and/or a water dispersible material and/or a water-soluble material. After using the pad comprised of these materials, it can be disposed into a toilet to flush, thereby the destruction of the pad can be easily and sanitarily achieved and the garbage in a toilet can be decreased.

In this Specification, "biodegradability" means that a substance is decomposed into gas such as carbon dioxide or methane, water, and biomass under anaerobic or aerobic condition according to the natural process under the existence of bacteria represented by actinomycetes and other microbes, and also means that the biodegradability (biodegradable rate and biodegradable degree) of the substance equals to a material naturally generated such as fallen leaves or a synthetic polymer generally recognized having the same biodegradability under the same environment. "Water dispersibility" means the same as water degradability, where there is no effect from the limited amount of water (menstrual blood) upon use, whereas in conditions of large amounts of water or under water flow, the fibers are easily dispersible into at least small pieces which cannot clog the toilet plumbing. "Water solubility" means the property of not being affected by limited amount of water (menstrual blood) upon use, but being soluble in large amounts of water or under a flow of water.

<Water Permeable Sheet>

A spun lace nonwoven fabric, a wetting-typed spun lace nonwoven fabric which fiber length is selected from 1 to 15 mm is eligible for materials to be used for a water permeable sheet. Further biodegradable resin by a water solution such as polylactic acid, polybutylene succinate and the like are eligible. For example, a melt blown nonwoven fabric mainly of polylactic acid in amount from 20 to 60 g/m² by a specific weight per unit in total mass of the component, a spun bond nonwoven fabric adjusted in amount of 15 to 30 g/m² and the fiber length of 1.1 to 3.3 dtex are eligible. Each nonwoven fabric material may be treated or not treated with perforation.

Other material is eligible that is acetate or a synthetic fiber of which single tow or tow of laminated continuous fibers is adjusted in amount from 50 to 300 g/m² and fibers are released from each other.

<Absorbent body>

A nonwoven fabric sheet obtained from needling is eligible for a material of the absorbent body. In consideration of biodegradability and the like of high polymer absorbing material, it is preferable to use carboxymethylcellulose fiber, or carboxyethylcellulose fiber.

<Non-water Permeable Sheet>

For non-water permeable sheet, PVA film, a film sheet which PVA film is treated one surface or both surfaces or partially with a silicone and the like, PVA film mixing of silicone, a starch film, a laminated paper of film and tissue and the like mainly of biodegradable resin such as polylactic acid or polybutylene succinate by a water solution are eligible. If required, a coloring by mixture of a pigment in amount from 0.1 to 5% of mass may be eligible.

In consideration of keeping a protection from a leak under too much humidity and protecting the tank from an exceeding load, a film mainly of polylactic acid is laminated with a tissue selected from a thickness of 10 to 20µ in an amount from 15 to 20 g/m² and a laminated paper which bonding area rate is provided in a range of 5 to 40% in laminating is eligible.

<Sheet Body>

A synthetic resin comprising the sheet body is made to be biodegradable or water soluble resin such as polylactic acid, polybuthylene succinate, PVA (polyvinylalcohol) resin and the like for having a structure with biodegradable and flushable by water. Further laminated materials of tissue and the biodegradable or water soluble resin are eligible.

<Connecting Method>

A single or a combination of a bonding by water soluble or water expanding polyvinylalcohol and the like, a heat seal, or a hydrogen bond connecting and the like are eligible of a method of connecting the sheet.

<Materials for Wrapping Container>

Conventional materials for a wrapping sheet are eligible for the wrapping container, for example, a polyethylene having a thickness of 15 to 60µ, polypropylene, polyester, polyvinyl alcohol, polylactic acid, polybutylene succinate, or nonwoven fabric, paper and these laminated materials. Specifically, a film mainly made of LDPE which is adjusted to being in a range from 15 to 30 g/m² by a specific weight per unit based on total mass of composition is eligible.

More specifically, in consideration of a sealing efficiency difficult to be interrupted by dust and a keeping ability of a wrapping condition, a compound nonwoven fabric comprising a spun bond, melt brown and spun bond in a range from 6 to 10 g/m², 5 to 20 g/m² and 6 to 10 g/m² by a specific weight per unit, a film and the like mainly made of LDPE selected from a density of 0.9 to 0.925 g/cm³ of which thickness is adjusted from 15 to 30μ are eligible. For a structure with biodegradability, water dispersibility and water solubility, nonwoven fabric or a film such as biodegradable polylactic acid, polyisocianete, a starch and the like are eligible, for water dispersible structure, a synthetic resin composition is eligible by altering a composition of biodegradable or water soluble polylactic acid, polybutylene succinate, polyvinylalcohol and the like. Further at the time of breaking off a seal, the wearer is urged to grip a wrapping body which interlabial pad is contained by one of hands, and it is preliminarily prevented to drop off interlabial pad from the wrapping body.

<Materials for Wrapping Container>

Materials for a wrapping sheet used for the wrapping container is not limited particularly, for example, a single of or laminated compound of tissue, nonwoven fabric and a film or are eligible.

Concretely a film mainly made of LDPE which is adjusted to being in a range from 15 to 30 g/m² by a specific weight per unit based on total mass of composition is eligible.

More embodied, in consideration of a sealing efficiency difficult to be interrupted by dust and a keeping ability of a wrapping condition, a compound nonwoven fabric comprising a spun bond, melt brown and spun bond in a range from 6 to 10 g/m², 5 to 20 g/m² and 6 to 10 g/m² by a specific weight per unit, a film and the like mainly of LDPE selected from a density of 0.9 to 0.925 g/cm³ of which thickness is adjusted from 15 to 30μ are eligible.

For a structure with biodegradability, water dispersibility and water solubility, nonwoven fabric or a film such as biodegradable polylactic acid, polyisocianete, a starch and the like are eligible, for water dispersible structure, a film mainly made of polyvinylalcohol, and a toilet paper are eligible. A synthetic resin composition is eligible by altering a composition of polylactic acid, polybutylene succinate, polyvinylalcohol and the like. More embodied, a laminated body of a film adjusted from polyisocianete in a range from 5 to 10 g/m² and a water soluble paper adjusted from 15 to 30 g/m² is eligible.

INDUSTRIAL APPLICABILITY

According to the present invention, the wearer inserts the fingertip into the fingertip insert opening which is provided on a side edge of the interlabial pad, thereby a body side surface of interlabial pad can be formed with a raised area which has a shape easily be along labia. During maintaining the condition of forming a raised area on the pad, the interlabial pad is attached into labia with a condition, thereby the pad can be arranged and engaged between labia in keeping the fingertip clean.

What is claimed is:

1. An interlabial pad having a longitudinal axis and a lateral axis, comprising:
    an absorbent body for absorbing body fluids;
    a surface side sheet and a rear surface side sheet enclosing said absorbent body;
    a holding sheet member lapped on the rear surface side sheet, the holding sheet member having bonded portions of the rear surface side sheet provided near each of two longitudinal surrounding ends of the interlabial pad and a pair of laterally opposed unbonded portions located at a rear surface side of the interlabial pad on left and right peripheral side edges near a central area along a longitudinal axis of the interlabial pad; wherein ends of the unbonded portions meet ends of the bonded portions along the peripheral side edges;
    a first fingertip insert opening formed by one of the pair of unbonded portions and arranged between the rear surface side sheet and the holding sheet member;
    a second fingertip insert opening formed by the other of the pair of unbonded portions and arranged between the rear surface side sheet and the holding sheet member; and
    a folding guide element along the longitudinal axis provided to form a convex protruding area linearly and continuously over the entire length of the longitudinal axis when the holding sheet member is pinched via the first and second fingertip insert openings.

2. The interlabial pad according to claim 1, wherein the folding guide element is provided in the absorbent body and is comprised of any of a broken line, a cut line, and a compression line.

3. The interlabial pad according to claim 1, wherein the interlabial pad has a size between 60 and 150 mm in the longitudinal direction of the longitudinal axis and a size of between 10 and 60 mm in a lateral direction, and the first and second fingertip insert opening each have a width of between 20 and 35 mm provided at a line symmetry position with respect to the longitudinal axis.

4. The interlabial pad according to claim 1, wherein a fingertip insert depth of each of the first and second fingertip insert openings is not less than 15 mm.

5. The interlabial pad according to claim 1, wherein the holding sheet member has a size not less than 80% in respect of a length size of the lateral direction of the interlabial pad.

6. The interlabial pad according to claim 1, wherein the holding sheet member has color, chromaticity and pattern different from those of the opposite side of the interlabial pad to the body side.

7. The interlabial pad according to claim 1, further comprising a long protruding area formed linearly and continuously over the entire length the longitudinal axis, wherein in using the pad, each fingertip of two fingers of the wearer is respectively inserted into one opening of the first and second fingertip insert openings, and thereafter the pad is folded at the longitudinal axis to be subject to use in a condition in which the long protruding area is further projected.

8. The interlabial pad according to claim 7, wherein the long protruding area is formed by unbonded portions of the holding sheet member provided in proximity to the longitudinal ends of the interlabial pad and folded along the longitudinal axis.

9. The interlabial pad according to claim 1, further comprising:
    a wrapping container to contain the interlabial pad,
    wherein the interlabial pad is contained such that the pair of fingertip insert openings are positioned in proximity to an unsealed portion of the wrapping container.

10. The interlabial pad according to claim 1, further comprising:
    a wrapping container to contain said interlabial pad,
    wherein the interlabial pad is folded in a mountain folded shape toward a body side along the longitudinal axis and is contained in the wrapping container.

* * * * *